United States Patent [19]

Murphy, II et al.

[11] Patent Number: 5,023,955
[45] Date of Patent: Jun. 18, 1991

[54] IMPACT-ABSORBING SOUND-ATTENUATING EARCUP

[75] Inventors: John A. Murphy, II; Charles A. Westgate, both of Carbondale, Pa.

[73] Assignee: Gentex Corporation, Carbondale, Pa.

[21] Appl. No.: 337,407

[22] Filed: Apr. 13, 1989

[51] Int. Cl.$^5$ ............................................. A41D 21/00
[52] U.S. Cl. ............................................. 2/209; 2/411; 2/423; 181/129
[58] Field of Search ............. 2/209, 423, 6, 411, 2/412; 181/129

[56] References Cited

U.S. PATENT DOCUMENTS

| | | | |
|---|---|---|---|
| 3,432,861 | 3/1969 | Flagg | 2/209 |
| 3,456,263 | 7/1969 | Aileo | 2/423 |
| 3,470,564 | 10/1969 | Aileo | 2/423 |
| 3,541,611 | 11/1970 | Beguin | 2/423 X |
| 3,686,691 | 8/1972 | Anderson | 2/209 |
| 3,784,984 | 1/1974 | Aileo | 2/423 |
| 3,805,298 | 4/1974 | Aho | 2/209 |
| 3,875,592 | 8/1975 | Aileo | 2/209 |
| 3,943,572 | 3/1976 | Aileo | 2/423 |
| 4,471,496 | 9/1984 | Gardner et al. | 2/209 |
| 4,905,322 | 3/1990 | Aileo et al. | 2/411 X |

Primary Examiner—Peter A. Nerbun
Attorney, Agent, or Firm—Shenier & O'Connor

[57] ABSTRACT

A sound-attenuating impact-absorbing earcup comprises a shell having a plurality of generally circular recesses adjacent to the periphery of the cup which function as stiffening contours. The stiffening contours increase the effective stiffness of the earcup shell, improving its sound attenuating capability, and also concentrate applied stress onto those portions of the stiffening contours nearest the point of applied stress. Sufficient applied force causes the shell to fracture in the areas of the stress concentrators, thereby to absorb impact energy in a controlled manner without transmitting it to the head of the wearer. To further enhance its sound-attenuating and impact-absorbing capabilities, the earcup is formed of a low-tensile-strength, high-elongation, high-loss-factor material such as polyvinyl chloride or similar polymer.

6 Claims, 3 Drawing Sheets

IMPACT-ABSORBING SOUND-ATTENUATING EARCUP

BACKGROUND OF THE INVENTION

This invention relates to an impact-absorbing sound-attenuating earcup assembly for use in a protective helmet or the like.

Earcup assemblies for attenuating ambient sound in noisy environments, such as in or around military helicopters or other aircraft, are well known in the art. Such assemblies are shown, for example, in Aileo U.S. Pat. Nos. 3,109,973, 3,470,564, 3,875,592 and 3,943,572, owned by the assignee herein. Currently available assemblies generally rely on the stiffness and surface density (i.e., mass per unit area) of the earcup to provide the desired sound attenuation. High stiffness and high surface density both decrease the amplitude of vibration of the earcup shell, thereby decreasing the noise inside the cup.

Current earcups provide good sound attenuation, but suffer from two limitations on their performance. First, in most lightweight aircraft helmets, the helmet is too small to avoid using the earcup as part of the crushing system that protects the head from impact. Most current cups are made with materials, thicknesses and shapes that make them too stiff to crush at low, nonlethal forces. Second, most commonly employed earcup materials are not well damped, and therefore resonance in the cup shell is not well controlled. Such resonances result in significant frequency-dependent drops in attenuation.

SUMMARY OF THE INVENTION

One object of our invention is to provide an earcup that satisfactorily attenuates ambient sound.

Another object of our invention is to provide an earcup that is dynamically stiff.

A further object of our invention is to provide an earcup that crushes at low impact forces.

Still another object of our invention is to provide an earcup that is free of resonances.

An additional object of our invention is to provide an earcup that is low in mass.

Other and further objects will be apparent from the following description.

One aspect of our invention contemplates providing the earcup shell with one or more stiffening contours, which for the purposes of this disclosure are defined as recesses that may be either inwardly formed or outwardly formed (and hence "protrusions" when viewed from outside the earcup) in an otherwise smooth surface portion of the shell. Not only do such contours add to a cup's stiffness, and hence sound-attenuating capability, but they also enhance its crush characteristics through the mechanism of stress concentration. More particularly, the bends of the stiffening contours that are closest to the source of stress function as stress concentrators, which severely disrupt the flow of stress in a direction normal to the axis of the bend. Each stiffening contour is designed to remain sufficiently geometrically stable to force material in the region of the stress concentrator to strain and ultimately fracture upon a predetermined impact load, so that the stiffening contour breaks away from the cup during impact at the location of the stress concentrator. Accordingly, by forming one or more stiffening contours so that they create stress concentrators in the path of stress experienced under impact, we achieve a structurally stiff cup shell for good sound attenuation characteristics. During impact, however, the forces exerted can be kept low enough to prevent potentially fatal head deceleration.

Although the stiffening contours described above may be used in conjunction with prior-art materials such ABS (acrylonitrile-butadiene-styrene) terpolymer, they are preferably combined with another aspect of our invention, which relates to the material itself. Thus, in accordance with another aspect of our invention, by changing the cup shell material from the ABS terpolymer standard in the industry to a material of low tensile strength and high elongation, we achieve a decrease in crush force while maintaining a high degree of energy absorption. Preferably, the tensile strength of the material should not be more than about 3000 pounds per square inch (psi), and the elongation not less that about 20%.

Typically, materials of this nature have a low stiffness, or, more formally, modulus of elasticity. Other things being equal, such a decrease in stiffness would result in a corresponding decrease in sound attenuation. Although the cup shell could be made thicker to compensate for this decrease in stiffness, such a thickened cup shell would be heavier and less crushable. Therefore, in accordance with a third aspect of our invention, to remedy this apparent problem we select a material having not only a low tensile strength and a high elongation, but also a high loss factor. Preferably, the loss factor should be at least 0.10 at 68° F. and at 1000 Hz. When sufficiently high, the loss factor, which increases the dynamic stiffness of the shell, damps cup shell vibrations at all frequencies and significantly reduces vibrations at resonant frequencies. This in turn implies a decrease in vibration transmission, and hence an increase in sound attenuation.

BRIEF DESCRIPTION OF THE DRAWINGS

In the accompanying drawings to which reference is made in the instant specification and which are to be read in conjunction therewith and in which like reference numerals are used to indicate like parts in the various views.

DESCRIPTION OF THE PREFERRED EMBODIMENT

Figure 2:
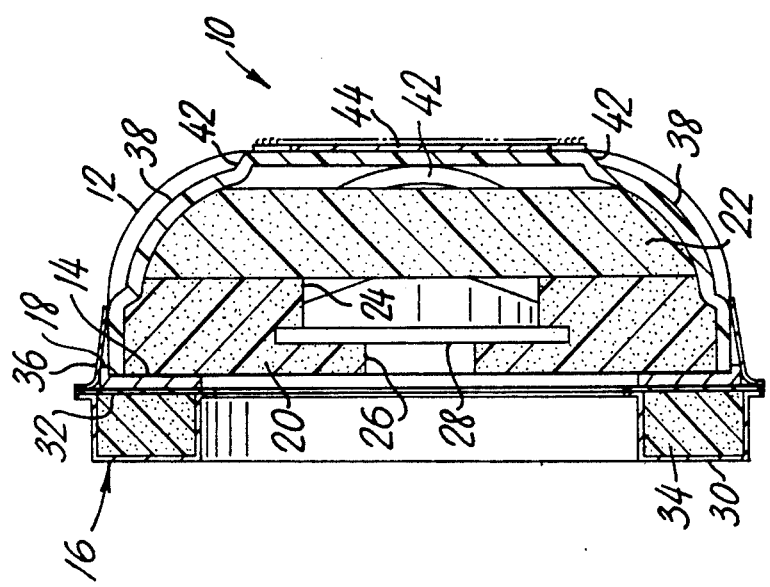
FIG. 2 is a section of the earcup assembly of FIG. 1, taken along line 2—2.
Figure 1:
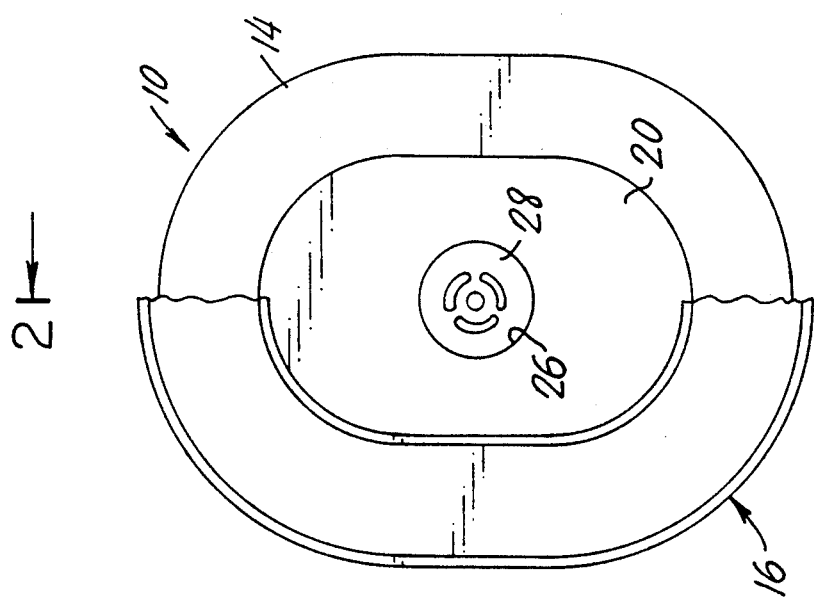
FIG. 1 is a left side elevation of a right earcup assembly constructed according to our invention, with parts broken away.

FIGS. 1 to 4 show a right earcup assembly 10 constructed according to our invention. The corresponding left earcup assembly is identical to or a mirror image of the right earcup assembly 10 and therefore has not been shown. Earcup assembly 10 includes a generally elliptical cup-shaped rigid shell 12 adapted to fit over a wearer's ear. A flange 14 extends inwardly from the periphery of the shell 12. An earseal 16 resiliently seals the region between the wearer's head and earcup 12 and flange 14.

Earcup shell 12, which is preferably about 0.09 inch thick, comprises a low-tensile-strength high-elongation, high-loss-factor material such as filled, flexible chloride (PVC) or similar polymer. Suitable materials are sold by the E.A.R. Division of Cabot Corporation under the trademark ISODAMP. Specific materials include ISODAMP C-2204-12, ISODAMP SD-12S and ISODAMP C-2003-12. Although shell 12 is shown as comprising a homogeneous material in the embodiment shown, the shell may also comprise a laminate having one or more damping layers. Shell 12 may be formed by any suitable method of molding, such as injection molding if the material is a thermoplastic such as PVC.

Earcup shell 12 is formed with a pair of generally circular recesses 38 with walls 42 at the top and bottom near its periphery, as well as with a pair of generally circular recesses 40 with walls 42 along the sides. Recesses 38 and 40 function a stiffening contours which increase the flexural rigidity, and hence sound attenuation, of the shell 12. In addition, the edge portions of walls 42 closest to the source of applied stress function as stress concentrators, which disrupt the flow of stress in the shell 12, thereby inducing fracture along such edge portions in response to a predetermined amount of impact force.

Figure 5:
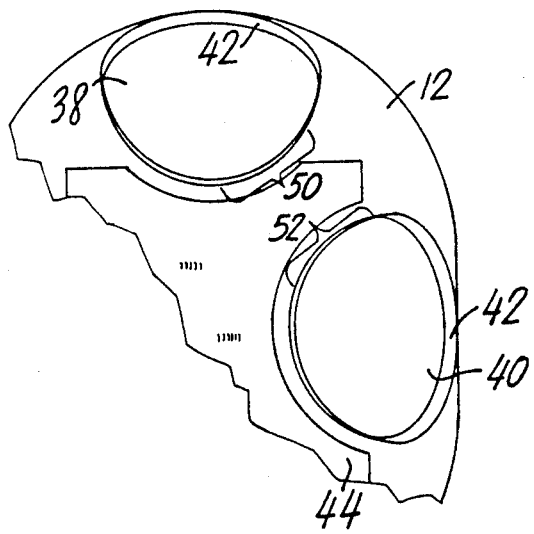
FIG. 5 is a fragmentary right side elevation of the earcup shown in FIG. 1 with the earseal and the earcup flange removed.

Thus, in response to an external force F (FIG. 4) applied normally at a center point P (FIG. 6) equidistant from recesses 38 and from recesses 40 as would typically be the case, adjacent edge portions 46 of recesses 38 and edge portions 48 of recesses 40 (FIG. 3) function as stress concentrators, inducing fracture along those edge portions of the recesses in response to a predetermined amount of applied force. Similarly, in response to an external force applied at a point equidistant from a recess 38 and adjacent recess 40, adjacent edge portions 50 and 52 of respective recesses 38 and 40 function as stress concentrators, inducing fracture along those portions in a similar manner (FIG. 5).

Figure 6:
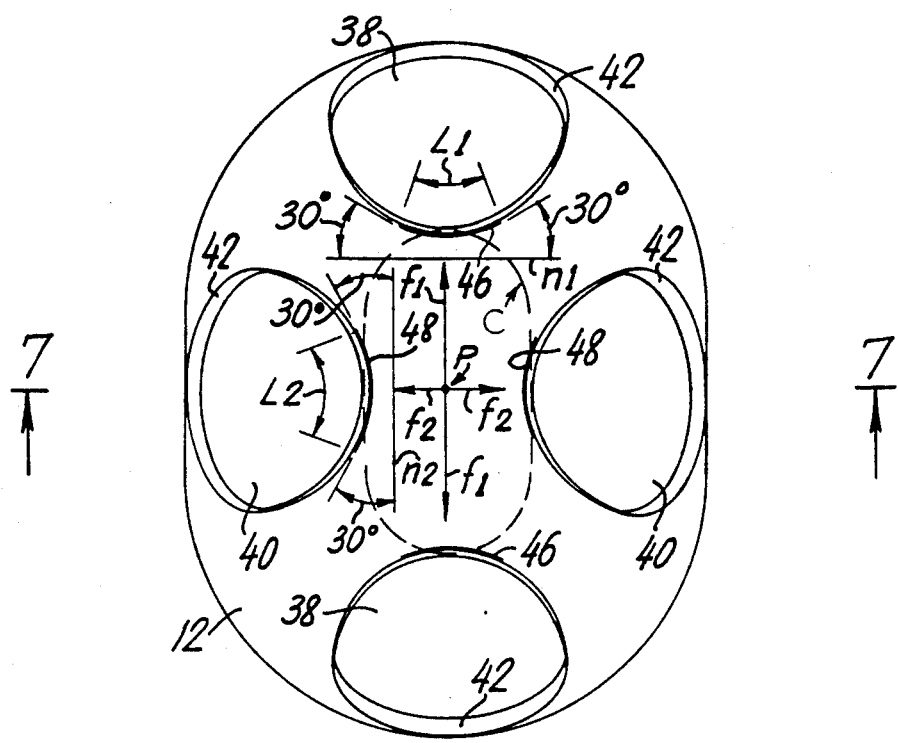
FIG. 6 is a right side elevation of the earcup shown in FIG. 1 with the earseal and the earcup flange removed.
Figure 7:
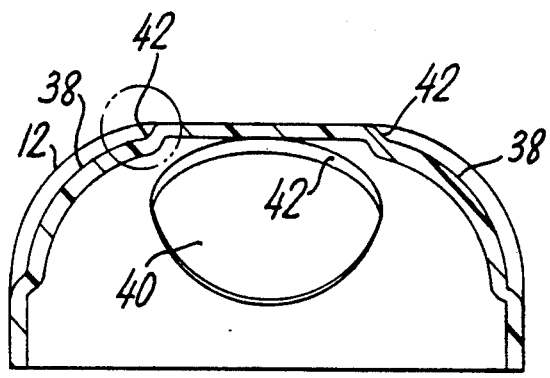
FIG. 7 is a section of the earcup shown in FIG. 6 along line, 7—7 thereof.
Figure 8:
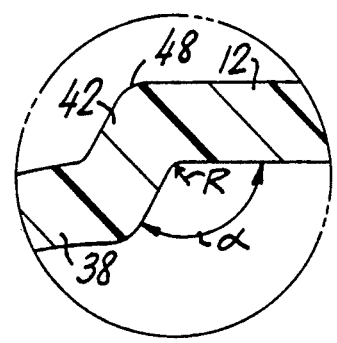
FIG. 8 is a greatly enlarged fragmentary section of the circled portion of FIG. 7.

Referring to FIGS. 6 to 8, the stiffening contours 38 and 40 and stress concentrators created by them should satisfy certain criteria in order to function effectively in accordance with our invention. First, the ratio of the effective lengths of the stress concentrators 46 and 48 for a force F (FIG. 5) applied at center point P (FIG. 6) to the area of the recesses 38 and 40 should meet or exceed a predetermined ratio—preferably about 0.12 inch of stress concentrator per square inch of the recesses 38 and 40. By "effective length" of the stress concentrator 46 is meant the arc length L1 of the stress concentrator along a portion (shown with thickened lines in FIG. 6) extending generally tangentially relative to and forming an angle of not more than 30° with a normal n1 to the direction of stress flow f1 from point P. Similarly, by "effective length" of the stress concentrator 48 is meant the arc length L2 of the stress concentrator along a portion (shown with thickened lines in FIG. 6) extending generally tangentially relative to and forming an angle of not more than 30° with a normal n2 to the direction of stress flow f2 from point P. Providing such a minimum ratio of length of the stress concentrators 46 and 48 to area of the recesses 38 and 40 forming the stiffening contours insures that the effect of the discontinuity of the stress concentrators will be substantial in comparison with that of the stiffening contours.

Second, the stress concentrators 46 and 48 should extend along a substantial portion of a closed curve C encircling the point P. More particularly, the combined effective lengths 2L1+2L2 of the stress concentrators 46 and 48 should comprise at least about 45% of the length of the closed curve C. This ensures that the stress concentrators 46 and 48 will have a significant effect on the overall cup strength.

Third, referring now to FIGS. 7 and 8, the walls 42 of the recesses 38 and 40 forming the stress concentrators 46 and 48 and the general surface contour of the shell 12 should define concave bends having a radius of curvature R of not more than about 0.010 inch. Fourth, and in conjunction with the third requirement, the angle α formed by the walls 42 with the inner surface of the earcup should be no more than about 135°. These requirements ensure a high degree of stress concentration.

Fifth, and finally, to assure easy splitting, the tensile strength of the material forming the earcup 12 should be no more than about 3000 pounds per square inch (psi).

Preferably, flange 14 is formed from 0.062-inch ABS terpolymer. Referring particularly to FIG. 2, flange 14 is formed with a lip 18 for receiving the periphery of the shell 12. Flange 14 also has a portion extending radially inwardly away from the peripheral portion to define a smaller-circumference aperture for receiving the wearer's ear as well as to provide a support for the earseal 16. If desired, the surface of the radially inwardly extending portion of flange 14 may be contoured in a manner complementary to that of the adjacent portion of the wearer's head as described in Aileo U.S. Pat. No. 3,875,592, the disclosure of which is incorporated herein by reference. Flange 14 is secured to shell 12 by any suitable means such as a layer of cement (not shown) applied along the interface between lip 18 and the periphery of shell 12.

Earseal 16, which has the elongated annular shape of flange 14, contains a layer of polyurethane foam 34 about 0.5 inch thick, preferably an energy-absorbing, slow-recovery foam such as Temper Foam Type T-38. Foam layer 34 is encased in an envelope formed from a base 32 and an outer cover 30 of 0.015-inch polyurethane film. Cover 30 is preformed in the shape shown in FIG. 2 and is bonded to base 32 along the inner and outer peripheries thermally or ultrasonically. An annular lip 36 bonded in a similar manner to the outer periphery of base 32 on the other side from cover 30 is stretched over the periphery of flange 14 to retain earseal 16 on the earcup-flange subassembly.

Earcup assembly 10 contains an earphone 28 of any suitable type known to the art. Earphone 28 fits within a complementary cutout 24 formed in an earphone pad 20 preferably comprising polyurethane foam. A circular aperture 26 formed in the front of earphone pad 20 provides a direct acoustical coupling between earphone 28 and the wearer's ear. A spacer pad 22 fills the interior of earcup shell 12 behind pad 24. Pads 20 and 24, shown in a compressed state in FIG. 2, are of uniform thickness when uncompressed and substantially of the shape of flange 14 as viewed in FIG. 1. Preferably pads 20 and 22 comprise high-porosity polyurethane foam to allow unrestricted transmission of sound from earphone 28 to the wearer.

Figure 3:
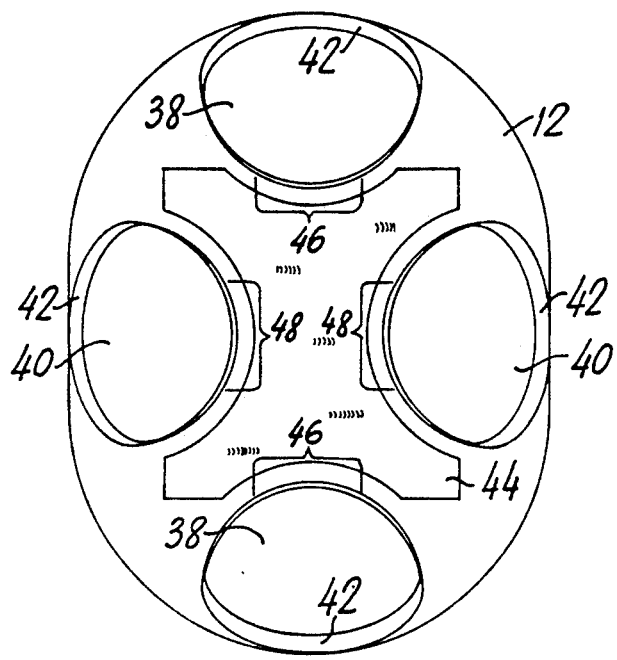
FIG. 3 is a right side elevation of the earcup assembly of FIG. 1 with the earseal and earcup flange removed.
Figure 4:
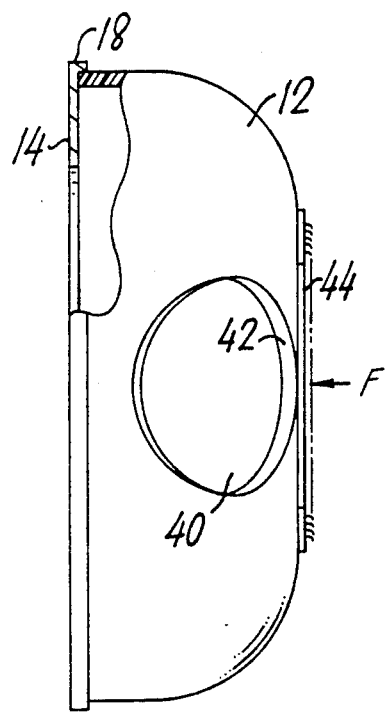
FIG. 4 is a rear elevation of the earcup assembly of FIG. 1 with the earseal and internal elements removed and with parts broken away.

Referring to FIGS. 2 to 4, earcup shell 12 also carries a strip 44 of pile fastener material, such as that sold under the trademark VELCRO, to permit assembly 10 to be releasably secured to a mating fastener inside the helmet shell, as shown, for example, in the copending application of J. A. Aileo et al, Ser. No. 182,851, filed Apr. 18, 1988, now U.S. Pat. No. 4,905,322, the specification of which is incorporated herein by reference. Alternatively, earcup shell 12 may carry a peripheral flange as shown in Aileo U.S. Pat. No. 3,470,564 or peripheral tabs as shown in said copending application to facilitate attachment to a helmet retention system.

It will be seen that we have accomplished the objects of our invention. Our earcup is dynamically stiff, and thus satisfactorily attenuates ambient sound, while at the same time being free of resonances. Further, our earcup is low in mass and crushes at low impact forces.

It will be understood that certain features and subcombinations are of utility and may be employed without reference to other features and combinations. This is contemplated by and within the scope of our claims. It is further obvious that various changes may be made in details within the scope of our claims without departing from the spirit of our invention. It is, therefore, to be understood that our invention is not to be limited to the specific details shown and described.

Having thus described our invention, what we claim is:

1. A sound attenuating earcup for insulating the ear of a wearer from ambient sound while inhibiting transmission to the wearer's head through the earcup of shocks of impact from severe bumps or the like which might otherwise injure the head of the wearer comprising a discrete hollow cup-shaped crushable shell forming a cavity for the wearer's ear to provide a sound-attenuating chamber around the ear, said shell having a periphery toward which stress resulting from a shock of impact travels along a path from a point of impact adjacent to the center of the shell, said shell being formed with stress concentrators, each of which has an appreciable extent in a direction across said path from said point of impact toward said periphery, said shell being formed of such a material and of such a thickness as to maintain its rigidity in ordinary use and to collapse upon impact from such severe bumps or the like to dissipate energy at an applied force less than that required to crush the skull of the wearer, said stress concentrators forming recesses in said shell, the surface of said shell having a center point, said recesses having edge portions extending generally tangentially relative to a line perpendicular to said path of stress resulting from a force applied at said point.

2. An earcup as in claim 1 in which said recesses are generally circular.

3. An earcup as in claim 1 in which said generally tangentially extending edge portions extend along a substantial portion of a closed curve surrounding said point.

4. An earcup as in claim 3 in which said generally tangentially extending edge portions comprise at least about 45% of the length of said curve.

5. An earcup as in claim 1 in which the ratio of the lengths of said portions to the area of said recesses is at least about 0.12 inch per square inch.

6. A sound-attenuating earcup as in claim 1 in which said shell is formed of a material having a tensile strength of not more than about 3,000 pounds per square inch, an ultimate elongation of not less than about twenty percent and a loss factor at least 0.10 at 68° F. and upon subjecting the earcup to sound energy at a frequency of 1,000 Hz and being of such a thickness as to maintain its rigidity in ordinary use and to collapse upon impact from such severe bumps or the like to dissipate energy at an applied force less than that required to crush the skull of the wearer.

* * * * *